US010611392B2

(12) United States Patent
Yang et al.

(10) Patent No.: US 10,611,392 B2
(45) Date of Patent: Apr. 7, 2020

(54) SHOPPING CART WITH STERILIZATION MECHANISM

(71) Applicant: Walmart Apollo, LLC, Bentonville, AR (US)

(72) Inventors: Feng Yang, Centerton, AR (US); Steven Jackson Lewis, Bentonville, AR (US); Matthew Dwain Biermann, Fayetteville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 152 days.

(21) Appl. No.: 15/849,950

(22) Filed: Dec. 21, 2017

(65) Prior Publication Data

US 2018/0178823 A1    Jun. 28, 2018

Related U.S. Application Data

(60) Provisional application No. 62/438,091, filed on Dec. 22, 2016.

(51) Int. Cl.
*B62B 5/06*    (2006.01)
*A61L 2/24*    (2006.01)
(Continued)

(52) U.S. Cl.
CPC .............. *B62B 5/069* (2013.01); *A61L 2/088* (2013.01); *A61L 2/10* (2013.01); *A61L 2/24* (2013.01);
(Continued)

(58) Field of Classification Search
CPC . B62B 5/069; B62B 3/14; H02S 10/40; A61L 2/088; A61L 2/10; A61L 2/24; A61L 2/28; A61L 2202/11; A61L 2202/14
(Continued)

(56) References Cited

U.S. PATENT DOCUMENTS 7,562,729 B2 * 7/2009 Hammerle .............. B60R 25/00
                                                         180/65.1
7,598,501 B2 * 10/2009 Jones .................... E05B 1/0069
                                                         250/455.11
(Continued)

FOREIGN PATENT DOCUMENTS

DE    102011112923 A1 *  3/2013    ............. A01N 25/10
DE    102011112923 A1     3/2013
(Continued)

OTHER PUBLICATIONS

Feng-Chyi Duh and „Jen-Chao Tai, Innovative Design of an Antibacterial Shopping Cart Attachment, 2015, Journal of Multidisciplinary Engineering Science and Technology (JMEST), vol. 2 Issue 10, Oct. 2015 http://www.jmest.org/wp-content/uploads/JMESTN42351112.pdf (Year: 2015).*
(Continued)

*Primary Examiner* — Ruth Ilan
*Assistant Examiner* — Hilary L Johns
(74) *Attorney, Agent, or Firm* — McCarter & English, LLP; David R. Burns

(57) ABSTRACT

A sterilization mechanism for a shopping cart is described. The shopping cart includes a frame, a basket portion mounted to the frame, and a handle portion mounted to the frame and including a top and bottom section. The shopping cart includes a cleanliness sensor configured to detect a cleanliness level of the handle portion. The shopping cart includes a sterilization mechanism for killing microorganisms on the handle portion detachably mounted to the handle portion. The sterilization mechanism includes an ultraviolet light source disposed within the body of the sterilization mechanism and configured to be actuated into a light-emitting position when the cleanliness level is detected to be equal to or above a predetermined cleanliness threshold. In the light-emitting position, the ultraviolet light source is
(Continued)

configured to emit ultraviolet light onto the handle portion to sterilize both the top and bottom sections of the handle portion from a mounted position.

20 Claims, 3 Drawing Sheets

(51) Int. Cl.
    *A61L 2/08*     (2006.01)
    *H02S 10/40*     (2014.01)
    *A61L 2/10*     (2006.01)
    *A61L 2/28*     (2006.01)
    *B62B 3/14*     (2006.01)

(52) U.S. Cl.
    CPC ................ *A61L 2/28* (2013.01); *H02S 10/40* (2014.12); *A61L 2202/11* (2013.01); *A61L 2202/14* (2013.01); *B62B 3/14* (2013.01)

(58) Field of Classification Search
    USPC .................................................... 280/33.992
    See application file for complete search history.

(56) References Cited

U.S. PATENT DOCUMENTS

| | | | |
|---|---|---|---|
| 8,114,346 B2 | 2/2012 | Hyde et al. | |
| 8,371,764 B2* | 2/2013 | Steverwald | ............... A45F 5/02 401/11 |
| 8,381,746 B2 | 2/2013 | Yoon et al. | |
| 2006/0076743 A1* | 4/2006 | Dunser | ................... B08B 9/023 280/33.992 |
| 2006/0267299 A1* | 11/2006 | Dunser | ................... B08B 9/023 280/33.992 |
| 2007/0267828 A1* | 11/2007 | Egizi | ...................... B62B 5/069 280/33.992 |
| 2009/0117001 A1* | 5/2009 | Hyde | ........................ A61L 2/10 422/24 |
| 2009/0193607 A1* | 8/2009 | Adell | ........................ A61L 2/10 15/246 |
| 2014/0011906 A1* | 1/2014 | Fosco, Jr. | .............. C09D 5/033 523/122 |
| 2016/0000951 A1* | 1/2016 | Kreiner | ................. A61L 2/0047 422/24 |

FOREIGN PATENT DOCUMENTS

| | | | |
|---|---|---|---|
| KR | 10-0743932 B1 | | 7/2007 |
| KR | 10-2007-0115314 A | | 12/2007 |
| KR | 20070115314 A | * | 12/2007 |
| KR | 10-2010-0132345 A | | 12/2010 |
| TW | 442961 U | * | 12/2012 |
| TW | M442961 U | | 12/2012 |

OTHER PUBLICATIONS

International Search Report and Written Opinion for Application No. PCT/US2017/067905, dated Feb. 16, 2018. 12 pages.
Sumitra, Teenagers Create Innovative Door Handle That Kills 99.8 Percent of Germs, http://www.odditycentral.com/pics/teenagers-create-innovative-door-handle-that-kills-99-8-percent-of-germs.html, last viewed Mar. 17, 2016.

* cited by examiner

SHOPPING CART WITH STERILIZATION MECHANISM

CROSS-REFERENCE TO RELATED APPLICATIONS

This application claims the benefit of commonly assigned U.S. Provisional Patent Application No. 62/438,091, which was filed on Dec. 22, 2016. The entire content of the foregoing provisional patent application is incorporated herein by reference.

BACKGROUND

Shopping carts are used by a large number of different customers in a retail establishment. The handle of the shopping cart is generally the section of the shopping cart with the most direct contact with the customer. Due to the extensive use of shopping carts throughout each day, microorganisms or germs can accumulate and grow on the handle. Anti-bacterial wipes may be provided to customers within the retail establishment to clean the handle (or any other portion) of the shopping cart.

SUMMARY

Exemplary embodiments of the present invention provide a shopping cart with a sterilization mechanism that is configured to kill microorganisms accumulating on the handle of the shopping cart. Rather than inconveniencing the customer by requiring the customer to locate anti-bacterial wipes to wipe down the handle of the shopping cart, the exemplary shopping cart includes a sterilization mechanism detachably mounted to the handle portion that is configured to emit ultraviolet light on all (or substantially all) of the surfaces of the handle portion when the shopping cart is not being used. The handle portion of the shopping cart can thereby be efficiently and conveniently cleaned one or more times throughout the day to prevent accumulation and growth of microorganisms or germs.

In one embodiment, an exemplary shopping cart includes a frame, a basket portion mounted to the frame, and a handle portion mounted to the frame or formed by the frame and including at least a top and bottom section. In some embodiments, the shopping cart includes a cleanliness sensor configured to detect a cleanliness level of the handle portion. The shopping cart includes at least one sterilization mechanism for killing microorganisms on the handle portion detachably mounted to the handle portion. The at least one sterilization mechanism includes a body configured to be mounted to the handle portion, and an ultraviolet light source disposed within the body of the sterilization mechanism and configured to be selectively or automatically actuated into a light-emitting position. For example, in some embodiments, the sterilization mechanism can be actuated into the light-emitting position manually. As a further example, in some embodiments, the sterilization mechanism can be automatically actuated into the light-emitting position when the cleanliness sensor detects the cleanliness level to be equal to or above a predetermined cleanliness threshold (e.g., based on the detected level of microorganisms). In the light-emitting position, the ultraviolet light source is configured to emit ultraviolet light onto the handle portion to sterilize both the top and bottom sections of the handle portion from a mounted position.

In one embodiment, a shopping cart sterilization system includes a shopping cart. The shopping cart includes a frame, a basket portion mounted to the frame, and a handle portion mounted to the frame or formed by the frame and including at least a top and bottom section. The shopping cart includes at least one sterilization mechanism for killing microorganisms on the handle portion detachably mounted to the handle portion. The at least one sterilization mechanism includes a body configured to be mounted to the handle portion, and an ultraviolet light source disposed within the body and configured to be selectively actuated into a light-emitting position. The shopping cart includes a cleanliness sensor configured to detect a cleanliness level of the handle portion, and a processing device equipped with a processor. The processing device is configured to execute instructions to actuate the ultraviolet light source into the light-emitting position when the cleanliness sensor detects the cleanliness level to be equal to or above a predetermined cleanliness threshold to emit ultraviolet light onto the handle portion to sterilize both the top and bottom sections of the handle portion.

In one embodiment, a method of sterilizing a shopping cart is provided. The shopping cart includes a frame, a basket portion mounted to the frame, and a handle portion mounted to the frame or formed by the frame, the handle portion including at least a top and bottom section. The method includes detachably mounting at least one sterilization mechanism to the handle portion for killing microorganisms on the handle portion. The at least one sterilization mechanism includes a body configured to be mounted to the handle portion, and an ultraviolet light source disposed within the body. The method includes detecting, with a cleanliness sensor affixed to the shopping cart, a cleanliness level of the handle portion. The method includes selectively or automatically actuating the ultraviolet light source into a light-emitting position when the cleanliness sensor detects the cleanliness level to be equal to or above a predetermined cleanliness threshold to emit ultraviolet light onto the handle portion to sterilize both the top and bottom sections of the handle portion.

It should be appreciated that combinations and/or permutations of embodiments are envisioned as being within the scope of the present invention. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

To assist those of skill in the art in making and using the disclosed shopping cart with sterilization mechanism, reference is made to the accompanying figures. The accompanying figures, which are incorporated in and constitute a part of this specification, illustrate one or more embodiments of the invention and, together with the description, help to explain the invention. In the figures.

DETAILED DESCRIPTION

It should be understood that certain relative terminology used herein, such as but not limited to, "front", "rear", "left", "top", "bottom", "vertical", "horizontal", "up" and "down" is solely for the purposes of clarity and designation and is not intended to limit embodiments to a particular position and/or orientation. Accordingly, such relative terminology should not be construed to limit the scope of the present invention. In addition, it should be understood that the scope of the present invention is not limited to embodiments having specific dimensions. Thus, any dimensions provided herein are for an exemplary purpose and are not intended to limit the invention to embodiments having particular dimensions.

Although retail establishments may clean the shopping carts at the end of each shopping day, microorganisms or germs still collect on the handle portion throughout the day and spread prior to washing of the shopping carts. Although retail establishments may provide anti-bacterial wipes for customers to wipe the handle portion of the shopping cart, this process requires the customer to locate the anti-bacterial wipe dispenser and clean the shopping cart properly prior to starting their shopping experience. Thus, the handle portion of the shopping cart generally remains dirty during use or requires the customer to spend additional time prior to shopping.

Exemplary embodiments of the present invention provide a shopping cart with a sterilization mechanism configured to kill microorganisms accumulating on the handle of the shopping cart when the shopping cart is not being used by the customer. Rather than inconveniencing the customer by requiring the customer to locate anti-bacterial wipes to wipe down the handle of the shopping cart, the exemplary shopping cart includes a sterilization mechanism detachably mounted to the handle portion that is configured to emit ultraviolet light on all (or substantially all) of the surfaces of the handle portion when the shopping cart is not being used. The handle portion of the shopping cart can thereby be efficiently and conveniently cleaned one or more times throughout the day to prevent accumulation and growth of microorganisms or germs.

Figure 1:
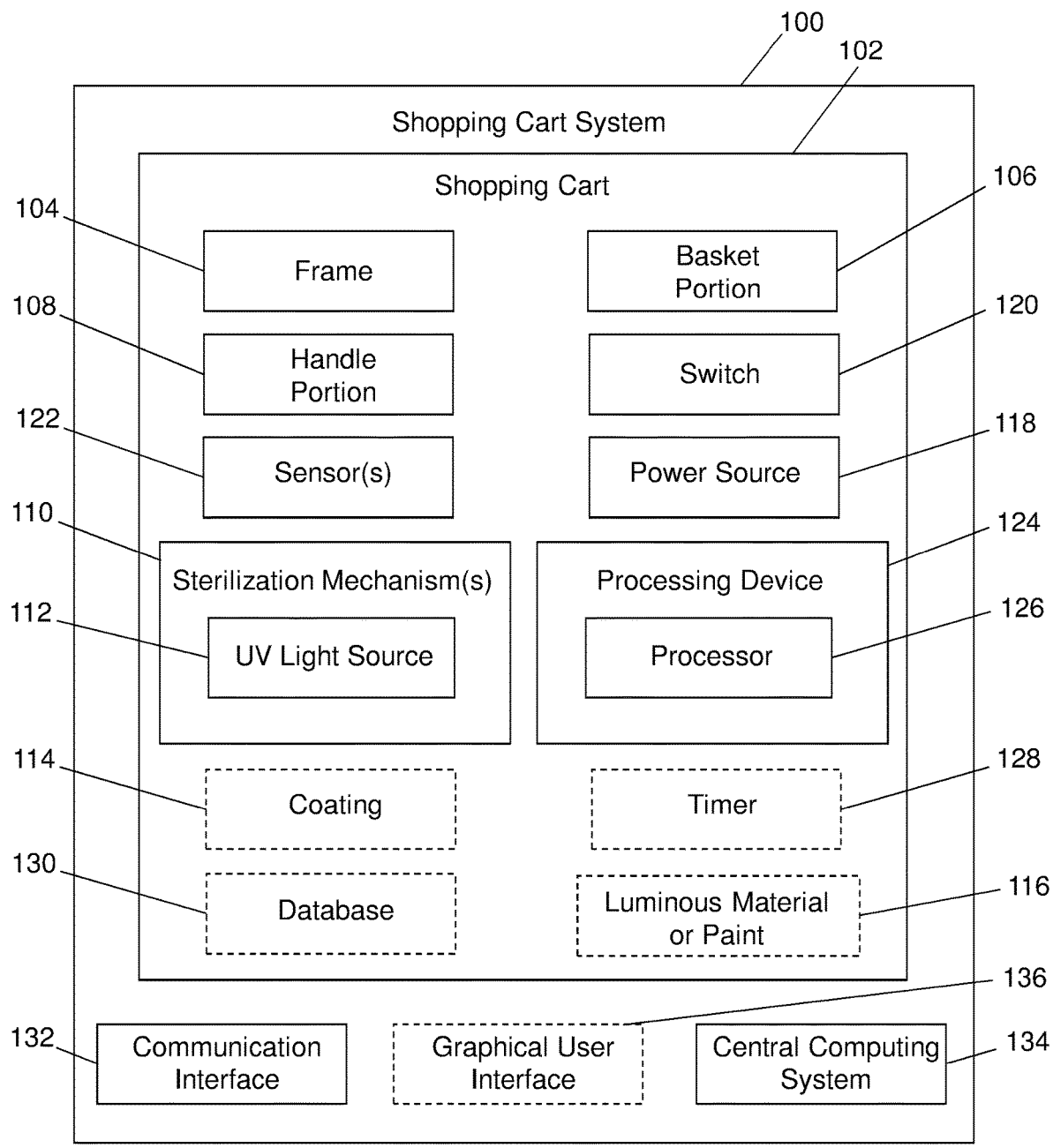
FIG. 1 is a block diagram of an exemplary shopping cart system in an embodiment.

FIG. 1 is a block diagram of an exemplary shopping cart system 100 (hereinafter "system 100") in accordance with exemplary embodiments. The system 100 includes one or more shopping carts 102. Each shopping cart 102 includes a frame 104 and a basket portion 106 mounted to the frame 104. The shopping cart 102 generally includes two pairs of wheels mounted to the frame 104 for transporting the shopping cart 102 within a geographic area. The shopping cart 102 includes a handle portion 108 either mounted to the frame 104 or formed by the frame 104. In one embodiment, the handle portion 108 can define a substantially cylindrical, elongated member having at least a top and bottom section.

The shopping cart 102 includes one or more sterilization mechanisms 110 for killing microorganisms on the handle portion 108 detachably mounted to the handle portion 108 (or to the frame 104 at a point adjacent to the handle portion 108). The sterilization mechanism 110 includes a housing or body configured and dimensioned to be detachably mounted to the handle portion 108. In one embodiment, the sterilization mechanism 110 can be positioned over and around one section of the handle portion 108, and a latch or clasp of the sterilization mechanism 110 can be used to engage opposing sides of the sterilization mechanism 110 to prevent the sterilization mechanism 110 from disengaging from the handle portion 108.

The sterilization mechanism 110 includes an ultraviolet (UV) light source 112 disposed within the housing or body of the sterilization mechanism 110. The UV light source 112 can be configured to be selectively actuated into a light-emitting position (e.g., a sterilization position) and an off position. In one embodiment, the sterilization mechanism 110 can define a substantially ring-like shape including an inner opening configured to surround a section of the handle portion 108 when mounted to the handle portion 108. In one embodiment, the UV light source 112 can include a plurality of light emitting diodes (LEDs) circumferentially or radially disposed within the ring-like shape of the housing to radially illuminate the top and bottom sections of the handle portion 108 with the UV light. In one embodiment, the LEDs can be radially spaced from each other. In one embodiment, the LEDs can be radially spaced adjacent to each other. The orientation of the LEDs is such that when in the light-emitting position, the UV light source covers substantially all of the outer surface of the handle portion 108 (e.g., the top and bottom sections).

In one embodiment, the handle portion 108 can define a substantially elongated structure including a distal end and a proximal end on opposing sides of the handle portion 108. The shopping cart 102 can include a first sterilization mechanism 110 detachably mounted at or near the distal end of the handle portion 108 and a second sterilization mechanism 110 detachably mounted at or near the proximal end of the handle portion 108. In such embodiments, the first and second sterilization mechanisms 110 can be configured to emit UV light in a single direction from the body (e.g., towards each other). Thus, in the light-emitting position, the UV light source 112 of the first sterilization mechanism 110 can emit UV light in the direction of the central portion of the handle portion 108 and the second sterilization mechanism 110, and the UV light source 112 of the second sterilization mechanism 110 can emit UV light in the direction of the central portion of the handle portion 108 and the first sterilization mechanism 110.

The UV light source 112 of the first sterilization mechanism 110 thereby illuminates at least a first half of the elongated structure of the handle portion 108, and the UV light source 112 of the second sterilization mechanism 110 illuminates at least a second half of the elongated structure of the handle portion 108. In one embodiment, the UV light source 112 emits light from the first and second sterilization mechanisms 110 beyond the central portion of the handle portion 108 such that the UV light from the respective UV light sources 112 overlap to ensure full coverage and sterilization of the outer surface of the handle portion 108.

In one embodiment, the handle portion 108 can define a substantially elongated structure including a distal end and a proximal end at opposing sides of the handle portion 108, and the body of at least one sterilization mechanism 110 can be detachably mounted at a substantially central position of the elongated structure between the distal and proximal ends. In such embodiments, the UV light source 112 includes LEDs on opposing sides of the body and can be configured to emit UV light in opposing directions from the sterilization mechanism 110. In the light-emitting position, the UV light source 112 emits UV light in opposing directions from the body to ensure full coverage of the first half of the elongated structure of the handle portion 108 with a first set of LEDs and full coverage of the second half of the elongated structure of the handle portion 108 with a second set of LEDs. In one embodiment, the shopping cart 102 can include a plurality of sterilization mechanisms detachably mounted along the elongated structure of the handle portion 108 and spaced from each other. It should be appreciated that although examples herein describe a UV light source that includes LEDs other types of UV light sources may be used without departing from the scope of the present invention.

In one embodiment, the handle portion 108 can include a coating 114 (e.g., a titanium dioxide coating, or the like) that covers substantially all of the outer surface of the handle portion 108 to assist in sterilizing the handle portion 108 with the UV light. In one embodiment, the handle portion 108 can be fabricated from a luminous material 116 or can be covered in a luminous paint 116 configured to exhibit luminescence in response to application of UV light from the UV light source 112. In particular, the level of luminescence exhibited by the luminous material or paint 116 can vary based on the time of application of the UV light on the handle portion 108. The different levels of luminescence can provide a visual indicator to a customer correlating with different levels of sterilization. A customer can thereby quickly choose a shopping cart 102 having the most sterilized handle portion 108.

The shopping cart 102 can include a power source 118 (e.g., a rechargeable battery, or the like) for connecting to, and providing electrical power to, the UV light source 112. In one embodiment, rotation of the wheels of the shopping cart 102 can be converted into electrical power to be stored in the power source 118 such that the shopping cart 102 can generate electrical power for operating the sterilization mechanism 110. In one embodiment, the shopping cart 102 can include an actuator or switch 120 for manually selectively actuating the UV light source 112 into the light-emitting position and the off position. In one embodiment, the shopping cart 102 can include one or more sensors 122 configured to detect characteristics associated with the shopping cart 102 and, based on the detected characteristics, a processing device 124 (including a processor 126) can execute the switch 120 to actuate the UV light source 112 into the light-emitting position.

In one embodiment, the sensor 122 can be a proximity sensor configured to detect the presence of the customer or individual near the handle portion 108. In response to a detected lack of presence of the individual near the handle portion 108 by the proximity sensor, the UV light source 112 can be configured to be actuated into the light-emitting position to emit UV light onto the handle portion 108. In response to a detected presence of the individual near the handle portion 108 by the proximity sensor, the UV light source 112 can be configured to be actuated into the off position to stop emitting UV light onto the handle portion 108.

In one embodiment, the sensor 122 can be a force sensor configured to detect a force imparted on the handle portion 108 (e.g., by one or both hands of the user). In response to the force sensor detecting a lack of force being imparted on the handle portion 108 over a certain time period, the UV light source 112 can be configured to be actuated into the light-emitting position to emit UV light onto the handle portion 108. In response to the force sensor detecting a force imparted on the handle portion 108, the UV light source 112 can be configured to be actuated into the off position.

In one embodiment, the sensor 122 can be an accelerometer configured to detect movement of the shopping cart 102. In response to the accelerometer detecting a lack of movement of the shopping cart 102 over a certain time period, the UV light source 112 can be configured to be actuated into the light-emitting position to emit UV light onto the handle portion 108. In response to the accelerometer detecting movement of the shopping cart 102, the UV light source 112 can be configured to be actuated into the off position. In one embodiment, the shopping cart 102 can include one or more databases 130 configured to electronically store data obtained from the sensor 122 and/or the sterilization mechanism 110, such as data relating to the use/movement of the shopping cart 102, the number of times the UV light source 112 is activated throughout each day, and the length of time the UV light source 112 is in the light-emitting position.

Thus, the sensor 122 ensures that the UV light source 112 is not actuated into the light-emitting position when the customer is using the shopping cart 102, and further ensures that the handle portion 108 is sufficiently sterilized when the shopping cart 102 is not in use. In one embodiment, the shopping cart 102 can include a timer 128 configured to actuate the UV light source 112 into the off position after the UV light source 112 has been in the light-emitting position for a predetermined amount of time. The predetermined amount of time can be selected as the time necessary to substantially sterilize the handle portion 108. The timer 128 can ensure that electrical power is conserved after the handle portion 108 has been thoroughly sterilized.

In one embodiment, the sensor 122 can be a cleanliness sensor configured to monitor and detect the cleanliness level of the surface of the handle portion 108. The cleanliness level can be determined based on a cleanliness index. The detected cleanliness level can be transmitted from the sensor 122 to the central computing system 134 (e.g., via a communication interface 132). If the detected cleanliness level is equal to or above a predetermined cleanliness threshold (e.g., a high threshold), the UV light source 112 can be automatically actuated into the light-emitting position to begin sterilization of the handle portion 108 (or actuated into the light-emitting position if the proximity sensor, force sensor and/or accelerometer indicate that the UV light source 112 is allowed to be actuated into the light-emitting position).

The sensor 122 can continue to detect and monitor the cleanliness level of the handle portion 108 at a preset frequency, providing a feedback loop to the central computing system 134 regarding the level of sterilization achieved. In some embodiments, the UV light source 112 can remain actuated in the light-emitting position until a predetermined cleanliness level is achieved and detected by the sensor 122 (e.g., a lower threshold). In some embodiments, the UV light source 112 can remain actuated in the light-emitting position for a predetermined amount of time or until the handle portion 108 is substantially sterilized. In some embodiments, the UV light source 112 can remain actuated in the light-emitting position until a signal is received from the proximity sensor, force sensor, and/or accelerometer indicating that the UV light source 112 should be turned off. The cleanliness sensor 122 can thereby monitor and create/modify the duty cycle of the UV light source 112 based on the detected need for sterilization.

In one embodiment, the system 100 can include a communication interface 132 configured to receive and transmit data from/to the central computing system 134. For example, the communication interface 132 can be configured to transmit data collected by the sensor 122 and stored in the database 130 to the central computing system 134 for processing. The system 100 can include a graphical user interface (GUI) 136 for input of data into the system 100 and for display of data from the database 130. In one embodiment, the GUI 136 can be used to input settings for the shopping cart 102, such as the intensity of UV light from the UV light source 112, the predetermined amount of time for the UV light source 122 to be in the light-emitting position as determined by the timer 128, combinations thereof, or the like.

Figure 2:
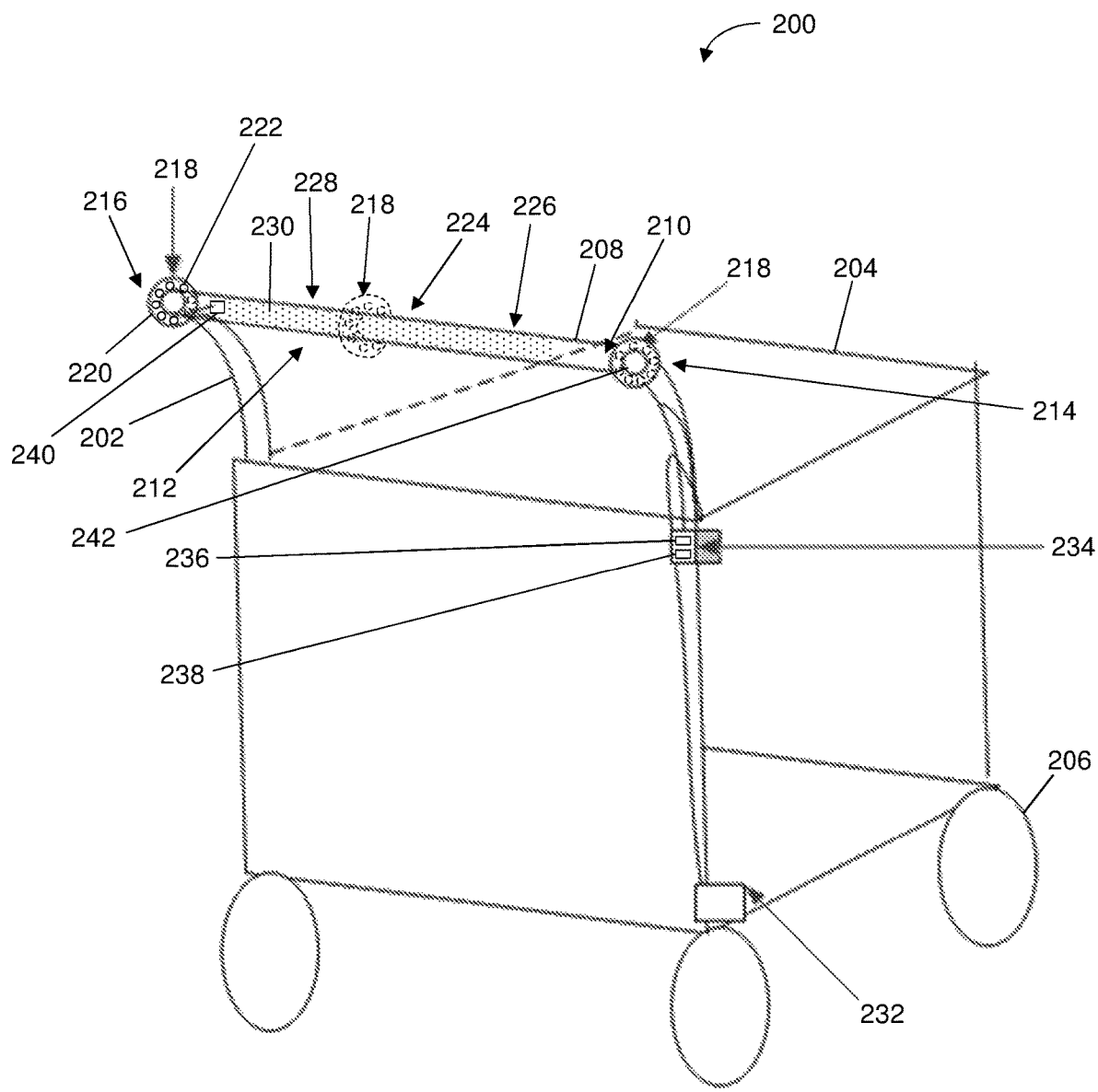
FIG. 2 is a diagrammatic perspective view of an exemplary shopping cart in an embodiment.

FIG. 2 is a diagrammatic perspective view of an exemplary shopping cart 200 in accordance with exemplary embodiments. The shopping cart 200 includes a frame 202 and a basket portion 204 mounted to the frame 202. The shopping cart 200 includes four wheels 206 mounted to the bottom of the frame 202. The shopping cart 200 includes a handle portion 208. In the embodiment shown in FIG. 2, the handle portion 208 is a separate, elongated member mounted between opposing sides of the frame 202. However, it should be understood that in some embodiments the handle portion 208 can be formed by the frame 202 itself. The handle portion 208 can define a substantially cylindrical form having a top section 210 and a bottom section 212. The top and bottom sections 210, 212, when combined, define the entire outer surface of the handle portion 208. The handle portion 208 includes a proximal end 214 and a distal end 216.

The shopping cart 200 includes one or more sterilization mechanisms 218 detachably mounted to the handle portion 208. The sterilization mechanism 218 includes a housing or body 220 and a plurality of UV light sources 222 (e.g., LEDs). The body 220 defines a substantially ring-like configuration with a central opening 242. The opening 242 allows the body 220 to fit around the handle portion 208 such that the sterilization mechanism 218 can be a separate component capable of being detachably mounted to any existing handle portion 208 of a shopping cart 200. The ring-like structure of the body 220 covers substantially 360° of the outer surface of the handle portion 208. The UV light sources 222 are circumferentially or radially disposed within the body 220 such that the entire outer surface of the handle portion 208 is illuminated in UV light when the UV light sources 222 are in the light-emitting position.

In one embodiment, one sterilization mechanism 218 can be mounted at the proximal end 214 with UV light sources 222 facing the distal end 216, and another sterilization mechanism 218 can be mounted at the distal end 216 with UV light sources 222 facing the proximal end 214. In such embodiments, the UV light sources 222 emit UV light in opposing directions only with the UV light sources 222 of the sterilization mechanism 218 at the proximal end 214 illuminating a first half 226 of the handle portion 208 up to at least a central position 224 and the UV light sources 222 of the sterilization mechanism 218 at the distal end 216 illuminating a second half 228 of the handle portion 208 up to at least the central position 224.

In one embodiment, the shopping cart 200 can include a single sterilization mechanism 218 detachably mounted at the central position 224 of the handle portion 208 with UV light sources 222 on opposing sides of the body 220. In particular, the UV light sources 222 can be directed in opposing directions such that one set of UV light sources 222 illuminates the first half 226 and another set of UV light sources 222 illuminates the second half 228. In one embodiment, the shopping cart 200 can include multiple sterilization mechanisms 218 spaced along the handle portion 208 (e.g. one sterilization mechanism 218 at the proximal end 214, one sterilization at the central position 224, and one sterilization at the distal end 216).

In one embodiment, the shopping cart 200 can include one or more features 230 on at least a portion of the outer surface of the handle portion 208. In one embodiment, the feature 230 can be a luminous material of fabrication or a luminous paint/film on the handle portion 208. The luminous material, paint or film exhibits different levels of luminescence based on the time of application of the UV light on the handle portion 208 to indicate the level of sterilization. For example, the longer the UV light is emitting on the handle portion 208, the stronger or brighter the glow of the luminous material, paint or film. In one embodiment, as a supplement to the sterilization mechanism 218, the feature 230 can be a coating (e.g., a titanium dioxide coating) on the handle portion 208 that accelerates sterilization when illuminated by UV light. For example, the luminous material can be a paint covering at least a portion of the handle portion 208 such that longer exposure to the UV light results in a stronger or brighter glow of the handle portion 208. The stronger or brighter glow provides a visual indicator of the cleanliness of the handle portion 208.

The shopping cart 200 can include a power source 232 for powering the UV light sources 222. The power source 232 can store electrical power generated from rotation of the wheels 206 and/or can be recharged from an external source. In one embodiment, the shopping cart 200 can include a solar power panel to generate and store electrical power in the power source 232. The shopping cart 200 can include a control panel 234. The control panel 234 can include an actuator or switch 236 for manually actuating the UV light sources 222 into the light-emitting position or the off position.

In one embodiment, the switch 236 can be actuated into an on position that allows the UV light sources 222 to actuate into the light-emitting position when one or more sensors 240 (e.g., force sensor, accelerometer, proximity sensor, combinations thereof, or the like) detect certain characteristics associated with the handle portion 208 and/or the shopping cart 200. The control panel 234 can include a timer 238 that indicates the time passed since the UV light sources 222 have been in the light-emitting position and/or the time remaining until the handle portion 208 is fully sterilized. In one embodiment, the timer 238 can actuate the UV light sources 222 into the off position after a predetermined period of time of having the UV light sources 222 in the light-emitting position (e.g., between approximately 30 seconds and approximately one minute). The predetermined period of time can be selected based on the time needed to substantially sterilize the entire outer surface of the handle portion 208 and conserve electrical power after the handle portion 208 has been sterilized.

In one embodiment, to prevent continuous UV light emission, a timer 238 can be utilized to prevent the UV light sources 222 from actuating into the light-emitting position sooner than, e.g., a fifteen minute time interval. For example, if the UV light sources 222 were in the light-emitting position and were actuated into the off position, the timer 238 can communicate with the control panel to send commands to prevent the UV light sources 222 from being actuated into the light-emitting position until fifteen minutes have passed (even if the characteristics detected by the sensor 240 indicate that the UV light sources 222 should be actuated into the light-emitting position). In one embodiment, the control panel 234 can include a display indicating how clean the handle portion 208 is (e.g., based on a cleanliness index).

Figure 3:
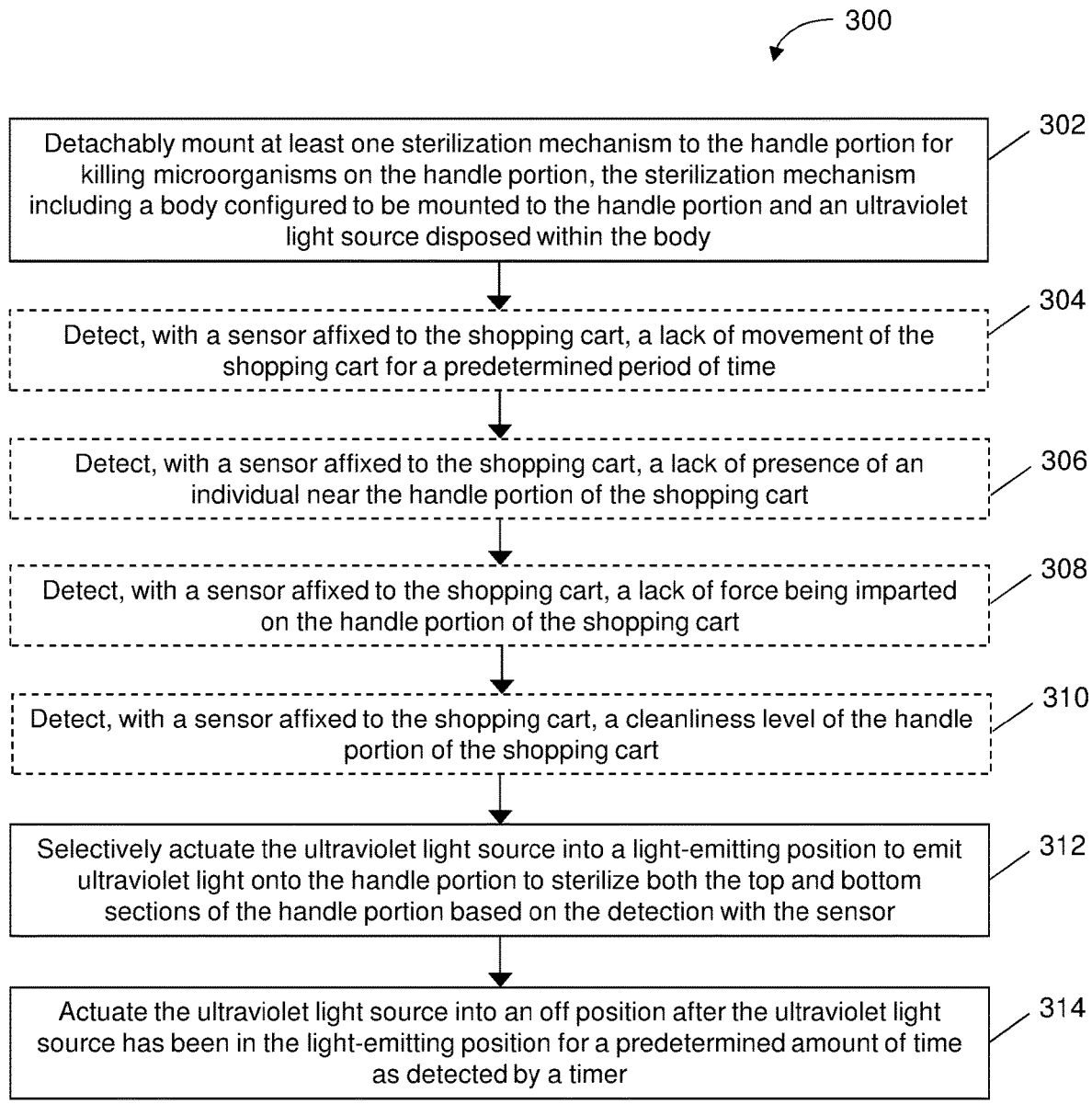
FIG. 3 is a flowchart illustrating a process of sterilizing a handle portion of a shopping cart in accordance with an embodiment.

FIG. 3 is a flowchart illustrating an exemplary process 300 of sterilizing a handle portion of a shopping cart with a sterilization mechanism. To begin, at step 302, at least one sterilization mechanism can be detachably mounted to the handle portion for killing microorganisms on the handle portion. The sterilization mechanism includes a body configured to be mounted to the handle portion and a UV light source disposed within the body. In embodiments having an accelerometer as a sensor, at step 304, a lack of movement of the shopping cart for a predetermined period of time can be detected with the sensor affixed to the shopping cart. In embodiments having a proximity sensor, at step 306, a lack of presence of an individual near the handle portion of the shopping cart can be detected with the sensor affixed to the shopping cart.

In an embodiment having one or more force sensors, at step 308, a lack of force being imparted on the handle portion of the shopping cart can be detected with the sensor affixed to the shopping cart. In embodiments having a cleanliness sensor, at step 310, a cleanliness level of the handle portion can be detected with the sensor affixed to the shopping cart. Based on one or more of the detections from the sensors, at step 312, the UV light source can be selectively actuated into a light-emitting position to emit UV light onto the handle portion to sterilize both the top and bottom sections of the handle portion. At step 314, the UV light source can be actuated into an off position after the UV light source has been in the light-emitting position for a predetermined amount of time as detected by a timer. It will be appreciated that different shopping carts may have different combinations of the described sensors or other sensors or may have only one type of sensor.

Thus, the exemplary shopping cart includes one or more sterilization mechanisms that actuate when the shopping cart is not in use to sterilize or kill microorganisms that generally accumulate on the handle portion of the shopping cart. The sterilization mechanism ensures that the handle portion is sterilized in-between uses by the same customer or different customers to prevent the spread of germs. The handle portion is thereby maintained in a clean state without the need for the customer to spend additional time in wiping the handle portion with anti-bacterial wipes, allowing the customer to focus on the shopping experience.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A shopping cart, comprising:
a frame;
a basket portion mounted to the frame;
a handle portion mounted to the frame or formed by the frame and including at least a top and bottom section; and
at least one sterilization mechanism for killing microorganisms on the handle portion detachably mounted to the handle portion, the at least one sterilization mechanism including:
(i) a body configured to be mounted to the handle portion, and
(ii) an ultraviolet light source disposed within the body of the sterilization mechanism and configured to be actuated into a light-emitting position;
wherein, in the light-emitting position, the ultraviolet light source is configured to emit ultraviolet light onto the handle portion to sterilize both the top and bottom section of the handle portion from a mounted position.

2. The shopping cart of claim 1, wherein the body of the at least one sterilization mechanism defines a ring shape configured to surround the handle portion when mounted, and wherein the light source includes a plurality of light-emitting diodes radially disposed within the ring shape of the body to radially illuminate the top and bottom section of the handle portion with ultraviolet light.

3. The shopping cart of claim 1, wherein:
the handle portion defines an elongated structure including a distal end and a proximal end and a first sterilization mechanism is detachably mounted at the distal end and a second sterilization mechanism is detachably mounted at the proximal end,
in the light-emitting position, the ultraviolet light source of the first sterilization mechanism emits ultraviolet light in the direction of the second sterilization mechanism and the ultraviolet light source of the second sterilization mechanism emits ultraviolet light in the direction of the first sterilization mechanism, and
the ultraviolet light source of the first sterilization mechanism illuminates at least a first half of the elongated structure of the handle portion, and the ultraviolet light source of the second sterilization mechanism illuminates at least a second half of the elongated structure of the handle portion.

4. The shopping cart of claim 1, wherein:
the handle portion defines an elongated structure including a distal end and a proximal end and the body of the at least one sterilization mechanism is detachably mounted at a central position of the elongated structure between the distal and proximal ends, and
in the light-emitting position, the ultraviolet light source emits ultraviolet light in opposing directions from the body of the at least one sterilization mechanism.

5. The shopping cart of claim 1, wherein the handle portion defines an elongated structure including a distal end and a proximal end and further comprising:
a plurality of sterilization mechanisms detachably mounted along the elongated structure of the handle portion.

6. The shopping cart of claim 1, further comprising:
a coating on the handle portion configured to assist in sterilizing the handle portion with the ultraviolet light, wherein the coating is a titanium dioxide coating.

7. The shopping cart of claim 1, wherein:
the handle portion includes a luminous material or paint configured to exhibit luminescence in response to application of the ultraviolet light from the ultraviolet light source, and
a level of luminescence exhibited by the luminous material or paint varies based on a time of application of the ultraviolet light.

8. The shopping cart of claim 1, further comprising a proximity sensor configured to detect a presence of an individual near the handle portion, wherein:
in response to a detected lack of presence of the individual near the handle portion by the proximity sensor, the ultraviolet light source is configured to be actuated into the light-emitting position to emit ultraviolet light onto the handle portion, and
in response to a detection of a presence of the individual near the handle portion, the ultraviolet light source is configured to be actuated into an off position.

9. The shopping cart of claim 1, further comprising:
a timer configured to actuate the ultraviolet light source into an off position after the ultraviolet light source has been in the light-emitting position for a predetermined amount of time.

10. The shopping cart of claim 1, further comprising a force sensor configured to detect a force imparted on the handle portion, wherein:
in response to the force sensor detecting a lack of force being imparted on the handle portion, the ultraviolet light source is configured to be actuated into the light-emitting position to emit ultraviolet light onto the handle portion; and
in response to the force sensor detecting a force imparted on the handle portion, the ultraviolet light source is configured to be actuated into an off position.

11. The shopping cart of claim 1, further comprising an accelerometer configured to detect movement of the shopping cart, wherein:
in response to the accelerometer detecting a lack of movement of the shopping cart, the ultraviolet light source is configured to be actuated into the light-emitting position to emit ultraviolet light onto the handle portion, and
in response to the accelerometer detecting movement of the shopping cart, the ultraviolet light source is configured to be actuated into an off position.

12. The shopping cart of claim 1, further comprising:
a switch configured to selectively actuate the ultraviolet light source between the light-emitting position and an off position.

13. The shopping cart of claim 1, further comprising:
a plurality of wheels; and
a power source configured to provide power to the at least one sterilization mechanism, the power source charged by rotation of the plurality of wheels.

14. The shopping cart of claim 1, further comprising:
a solar panel; and
a power source configured to provide power to the at least one sterilization mechanism, the power source charged by the solar panel.

15. The shopping cart of claim 1, comprising a cleanliness sensor configured to detect a cleanliness level of the handle portion, wherein the ultraviolet light source is configured to be actuated into the light-emitting position when the cleanliness sensor detects the cleanliness level to be equal to or above a predetermined cleanliness threshold.

16. The shopping cart of claim 15, comprising a feedback loop of the cleanliness sensor configured to regulate actuation of the ultraviolet light source between the light-emitting position and an off position based on the detected cleanliness level.

17. A shopping cart sterilization system, comprising:
a shopping cart including:
a frame;
a basket portion mounted to the frame; and
a handle portion mounted to the frame or formed by the frame and including at least a top and bottom section;
at least one sterilization mechanism for killing microorganisms on the handle portion detachably mounted to the handle portion, the at least one sterilization mechanism including:
a body configured to be mounted to the handle portion;
an ultraviolet light source disposed within the body and configured to be selectively actuated into a light-emitting position;
a cleanliness sensor configured to detect a cleanliness level of the handle portion; and
a processing device equipped with a processor,
wherein the processing device is configured to execute instructions to actuate the ultraviolet light source into the light-emitting position when the cleanliness sensor detects the cleanliness level to be equal to or above a predetermined cleanliness threshold to emit ultraviolet light onto the handle portion to sterilize both the top and bottom section of the handle portion.

18. The system of claim 16, comprising at least one of a proximity sensor configured to detect a presence of an individual near the handle portion, and a force sensor configured to detect a force imparted on the handle portion.

19. The system of claim 16, comprising an accelerometer configured to detect movement of the shopping cart.

20. A method of sterilizing a shopping cart, the shopping cart including a frame, a basket portion mounted to the frame, and a handle portion mounted to the frame or formed by the frame, the handle portion including at least a top and bottom section, the method comprising:
detachably mounting at least one sterilization mechanism to the handle portion for killing microorganisms on the handle portion, the at least one sterilization mechanism including:
a body configured to be mounted to the handle portion;
an ultraviolet light source disposed within the body;
detecting, with a cleanliness sensor affixed to the shopping cart, a cleanliness level of the handle portion; and
actuating the ultraviolet light source into a light-emitting position when the cleanliness sensor detects the cleanliness level to be equal to or above a predetermined cleanliness threshold to emit ultraviolet light onto the handle portion to sterilize both the top and bottom sections of the handle portion.

\* \* \* \* \*